United States Patent [19]

Tan et al.

[11] Patent Number: 4,909,631

[45] Date of Patent: Mar. 20, 1990

[54] METHOD FOR FILM THICKNESS AND REFRACTIVE INDEX DETERMINATION

[76] Inventors: Raul Y. Tan, 1528 Fujiko Dr., San Jose, Calif. 95131; David W. Myers, 773 Carla St.; Robert G. Ozarski, 2653 Klamath, both of Livermore, Calif. 94550; John F. Schipper, 3133 Flowers, Palo Alto, Calif. 94306; Michael P. C. Watts, 1185 LosTrancos Rd., Portola Valley, Calif. 94025

[21] Appl. No.: 134,638

[22] Filed: Dec. 18, 1987

[51] Int. Cl.⁴ .................................................. G01B 11/06
[52] U.S. Cl. ..................................... 356/382; 356/128; 356/357
[58] Field of Search ................. 356/128, 357, 381, 382; 364/563

[56] References Cited

U.S. PATENT DOCUMENTS

| | | | |
|---|---|---|---|
| 3,892,490 | 7/1975 | Uetsuki et al. | 356/382 |
| 4,498,772 | 2/1985 | Jastrzebski et al. | 356/382 |
| 4,645,349 | 2/1987 | Tabata | 356/382 |
| 4,676,647 | 6/1987 | Kikkawa et al. | 356/382 |

Primary Examiner—Richard A. Rosenberger
Attorney, Agent, or Firm—John F. Schipper; Harold Huberfeld

[57] ABSTRACT

Two methods for determination of thickness of a film of known material that is mounted on one face of a solid substrate of known material are disclosed, using: (1) inversion of an optical beam reflectivity equation; or (2) determination of the film thickness that minimizes the variance of the optical beam reflectivity, computed at each of a predetermined sequence of optical beam wavelengths. Four methods for determination of the (real) refractive index of a film of known thickness mounted on a face of a solid substrate of known material are disclosed, using: (1) minimization of absolute differences of computed and measured optical beam reflectivity, summed over a sequence of known film thicknesses, for assumed values of the refractive index; (2 and 3) two iterative techniques of promote convergence of an estimate of the index to a final value of the refractive index; or (4) solution of a quadratic equation whose coefficients are slowly varying functions of the solution variable.

7 Claims, 1 Drawing Sheet

METHOD FOR FILM THICKNESS AND REFRACTIVE INDEX DETERMINATION

FIELD OF THE INVENTION

This invention relates to determination of the thickness of a film of at least partially transparent material by use of thin film interference techniques.

BACKGROUND OF THE INVENTION

Measurement of the (unknown) thickness of a film of material, which is mounted on one of its flat faces on a solid substrate of different material, is a continuing problem in materials science. The film may have certain mechanical, electrical, magnetic or optical properties that vary with film thickness so that accurate determination of film thickness is necessary before one can predict the response of the film/substrate combination. Uniformity of film thickness may be a goal so that measurements of film thickness at a number of locations must be made to confirm or refute the assumption that film thickness is substantially uniform.

SUMMARY OF THE INVENTION

One object of the invention is to provide a method for determining relatively quickly and accurately the thickness of a film of material mounted on a solid substrate of a different material, using reflectivity measurements at a plurality of wavelengths at which the film is at least partially transparent.

Other objects and advantages of the method are disclosed in the detailed description and accompanying drawings.

Given a predetermined thickness range of interest ($t_{min} \leq t \leq t_{max}$) and a film of material with predetermined indices of refraction $n_2 = n_2(\lambda_j)$ ($j = 1, 2, \ldots, w$) at a plurality of $w (\geq 2)$ distinct wavelengths of a light beam used to illuminate the film, where the film is at least partially transparent at each of these wavelengths, where the film is attached on one of its faces to a solid substrate of predetermined material having predetermined indices of refraction $n_3 = n_3(\lambda_j)$ at the plurality of wavelengths, where the coefficient of amplitude reflection for a light beam of polarization index $k (= p$ for a p-polarization wave and $= s$ for an s-polarization wave), incidence angle $\theta_1'$ and transmission angle $\theta_2'$ of a light beam of wavelength $\lambda_j$ traveling in a vacuum toward the film-vacuum interface is a predetermined number $r_{12} = r_{12,k}(\theta_1', \theta_2'; \lambda_j)$ for each wavelength $\lambda_j$, and where the coefficient of amplitude reflection for a light beam of polarization index $k (= p, s)$, incidence angle $\theta_2'$ and transmission angle $\theta_3'$ of a light beam of wavelength $\lambda_j$ traveling in the film material toward the substrate-film interface is a predetermined number $r_{23} = r_{23,k}(\theta_2', \theta_3'; \lambda_j)$ for each wavelength $\lambda_j$, a method for achieving the foregoing and other objects is provided, in one embodiment, that comprises: (1) directing a beam of light of polarization index $k (= p$ or $s)$ at each wavelength $\lambda_j$ ($j = 1, 2, \ldots, w$) at a predetermined, nonnegative incidence angle $\theta_1$ within a vacuum or air at the exposed face of the film; (2) measuring the reflectivities $R_j = R(\theta_1; \lambda_j)$ of the light beam intensity at the exposed face of the film at each wavelength $\lambda_j$; (3) determining the Permitted Set Of Pairs of integers $(k_j, m_j)$ corresponding to the wavelength $\lambda_j$ and the thickness range of interest according to the relations $$m_j = [0.5 + \gamma_j],$$

$$k_j = (-1)^{[2\gamma_j]},$$

$$\gamma_j = \frac{2n_2(\lambda_j)}{\lambda_j} t \cos\theta_2, \quad (t_{min} \leq t \leq t_{max})$$

$$\cos\theta_2 = \left(1 - \frac{\sin^2\theta_1}{n_2(\lambda_j)^2}\right)^{\frac{1}{2}},$$

where $[x]$ denotes the integral part of the real number $x$; (4) determining an array of thicknesses $t(\lambda_j; k_j; m_j)$ for each of the wavelengths $\theta_j$ ($j = 1, 2, \ldots, w$) according to the relations $$t(\lambda_j; k_j; m_j) = \frac{\lambda_j}{4\pi n_2(\lambda_j)\cos\theta_2} \left[k_j \cos^{-1}\left(\frac{R_j(1 + r_{12}^2 r_{23}^2) - r_{12}^2 - r_{23}^2}{2(1 - R_j)r_{12}r_{23}}\right) + 2\pi m_j\right],$$

$$\sin\theta_1 = n_2 \sin\theta_2 = n_3 \sin\theta_3,$$

$$r_{12} = r_{12,k}(\theta_1, \theta_2; \lambda_j),$$

$$r_{23} = r_{23,k}(\theta_2, \theta_3; \lambda_j),$$

where the pair $(k_j, m_j)$ of integers is varied over the Permitted Set Of Pairs for the wavelength $\lambda_j$ and the predetermined thickness range; (5) for each w-tuple of thicknesses $[t(\lambda_1; k_1, m_1), t(\lambda_2; k_2, m_2), \ldots, t(\lambda_w; k_w, m_w)]$ determined as above, determining the statistical mean $\mu_t$ and standard deviation $\sigma_t$ for the w-tuple of thickness numbers; (6) choosing the thickness w-tuple that produces the smallest standard deviation $\sigma_t$ among the sequence of such w-tuples and designating the mean $\mu_t$ of that thickness w-tuple as the thickness $t$ of the film.

In a second embodiment, a method is provided that comprises, under the same assumptions as above: (1) same as step no. (1) in first embodiment; (2) same as step no. (2) in first embodiment; (3) choosing an array of film thickness values $t_1, t_2, \ldots, t_m$ with $t_{min} \leq t_1 < t_2 < \ldots < t_M \leq t_{max}$; (4) generating an array $R(\theta_1; \lambda_j; t_s)$ of computed reflectivity numbers for each wavelength $\lambda_j$ ($j = 1, 2, \ldots, w$) and each film thickness $t_s$ ($s = 1, 2, \ldots M$) according to the relations $$R(\theta_1; \lambda_j; t_s) = \frac{r_{12}^2 + 2r_{12}r_{23}\cos\beta + r_{23}^2}{1 + 2r_{12}r_{23}\cos\beta + r_{12}^2 r_{23}^2},$$

$$\beta = \beta_{js} = \frac{4\pi n_2(\lambda_j)t_s}{\lambda_j} \cos\theta_2,$$

$$\sin\theta_1 = n_2\sin\theta_2 = n_3\sin\theta_3,$$

$$r_{12} = r_{12,k}(\theta_1, \theta_2; \lambda_j),$$

$$r_{23} = r_{23,k}(\theta_2, \theta_3; \lambda_j);$$

(5) forming an array of variance numbers $$\chi_R(t_s) = \frac{1}{w} \left[ \sum_{j=1}^{w} (R(\theta_1;\lambda_j;t_s) - R(\theta_1;\lambda_j))^2 \right]^{\frac{1}{2}}$$

for each thickness $t_s$ in the array of thicknesses (s=1,2, ..., M); and (6) choosing as the thickness t of the film the value $t_s$ from the array of film thicknesses for which the variance $\chi_R(t_s)$ is a minimum.

DESCRIPTION OF THE PREFERRED EMBODIMENTS

Figure 1:
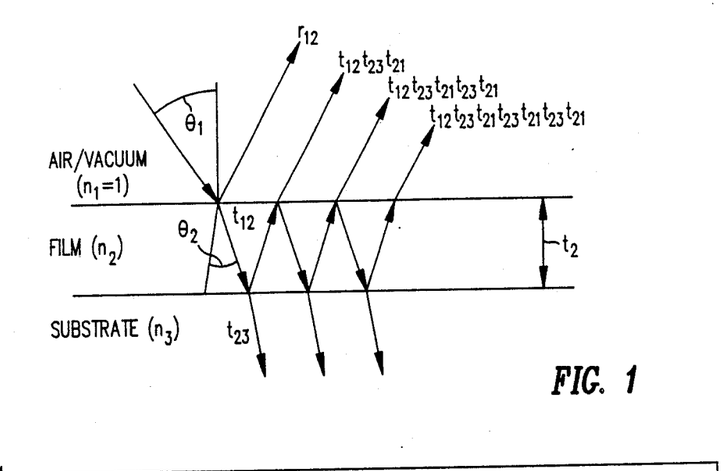
FIG. 1 is a graphic view of the interference produced by reflection of a plurality of light rays at the interfaces of a film of one material mounted on a solid substrate of a different material.

Where a ray of light is incident upon a (partially or fully transparent) film of material that is mounted at one of the film faces on a solid substrate, multiple reflections occur in a well known manner at the (air/vacuum)-film interface and at the film-substrate interface. This is illustrated in FIG. 1, where a ray of light of wavelength λ is incident on the exposed film face at an incidence angle $\theta_1 > 0$. As is customary, the situation with $\theta_1 = 0$ is referred to herein as normal incidence. In FIG. 1, the numbers $n_1$, $n_2$ and $n_3$ label the indices of refraction in air or vacuum ($n_1$), the film material ($n_2$) and the substrate material ($n_3$), all of which may vary with the wavelength λ of the incident light. For the vacuum/film/substrate configuration shown in FIG. 1, the treatment of multiple beam interference fringes produced in a plane parallel plate presented in M. Born and J. Wolf, *Principles of Optics*, Pergomon Press, Oxford, Fifth Ed. (1975), pp. 36-42 and 323-326, may be extended to include reflection from the substrate backing. The result is that the reflectivity R of the p-polarization (p) and s-polarization (s) components of intensity of the light ray in FIG. 1 are given by $$R(\theta_1;\lambda;t) = \frac{r_{12}^2 + r_{23}^2 + 2r_{12} r_{23}\cos\beta}{1 + 2r_{12}r_{23}\cos\beta + r_{12}^2 r_{23}^2} \quad (1)$$

where $$r_{12,p} = r_{12,p}(\theta_1,\theta_2;\lambda) = \frac{n_2\cos\theta_1 - n_1\cos\theta_2}{n_2\cos\theta_1 + n_1\cos\theta_2},$$

$$r_{23,p} = r_{23,p}(\theta_2,\theta_3;\lambda) = \frac{n_3\cos\theta_2 - n_2\cos\theta_3}{n_3\cos\theta_2 + n_2\cos\theta_3},$$

$$r_{12,s} = r_{12,s}(\theta_1,\theta_2;\lambda) = \frac{-n_2\cos\theta_2 + n_1\cos\theta_1}{n_2\cos\theta_2 + n_1\cos\theta_1},$$

$$r_{23,s} = r_{23,s}(\theta_2,\theta_3;\lambda) = \frac{-n_3\cos\theta_3 + n_2\cos\theta_2}{n_3\cos\theta_3 + n_2\cos\theta_2},$$

are the amplitude reflection coefficients for polarization index k=p (p-polarization) and for polarization index k=s (s-polarization) and $$n_1 \sin\theta_1 = n_2 \sin\theta_2 = n_3 \sin\theta_3, \quad (2)$$

$\theta_i$ = light ray angle in medium no. i relative to normal (i=1, 2, 3), $$\beta = 4\pi n_2(\lambda)t \cos\theta_2/\lambda, \quad (3)$$

t = film thickness,
λ = wavelength of incident light ray.

It is assumed that the substrate is sufficiently thick or sufficiently absorbing or scattering that substantially no light that is refracted into the substrate returns to the film-substrate interface. For the initial air/vacuum medium, $n_1 \doteq 1$. It should be kept in mind that R refers to the reflectivity associated with a component of the light ray that oscillates either parallel (p) or perpendicular (s) to the plane of incidence and that R varies with wavelength λ and with the incidence angle $\theta_1$; the refraction angles $\theta_2$ and $\theta_3$ are determinable from $\theta_1$ using Eq. (2).

For measurements with absorption in the film material, Eq. (1) becomes $$R = \frac{r_{12}^2 + r_{23}^2 e^{-2\alpha L} + 2r_{12}r_{23}e^{-\alpha L}\cos\beta}{1 + r_{12}^2 r_{23}^2 e^{-2\alpha L} + 2r_{12}r_{23}e^{-\alpha L}\cos\beta} \quad (4)$$

where
α = absorption coefficient (cm$^{-1}$)
L = optical path length in film = 2t sec$\theta_2$
By rearranging the terms and placing the term that contains the thickness variable on the left hand side of the equation, one obtains $$\cos\left(\frac{4\pi n_2 t \cos\theta_2}{\lambda}\right) = \quad (5)$$

$$\frac{R(1 + r_{12}^2 r_{23}^2 e^{-\alpha L}) - (r_{12}^2 + r_{23}^2 e^{-2\alpha L})}{2(1 - R) r_{12}r_{23}e^{-\alpha L}}$$

By taking the inverse cosine of both sides of the equation, one obtains $$\frac{4\pi n_2 t \cos\theta_2}{\lambda} = \quad (6)$$

$$\cos^{-1}\left(\frac{R(1 + r_{12}^2 r_{23}^2 e^{-2\alpha L}) - (r_{12}^2 + r_{23}^2 e^{-2\alpha L})}{2(1 - R) r_{12}r_{23}e^{-\alpha L}}\right) + 2\pi m$$

However, there will be instances when Eq. (6) cannot be satisfied with any value of m. This occurs when the left hand side of the equation falls in the third or fourth quadrant, π to 2π; the inverse cosine function always returns values from in the range [0,π] because of the function's symmetry with the x-axis. To compensate for this shortcoming, a variable k is introduced in the inverse cosine term and can only have values 1 or −1, with k=−1 corresponding to the range (π,2π) for the inverse cosine function. Eq. (6) then becomes $$\frac{4\pi n_2 t \cos\theta_2}{\lambda} = \quad (7)$$

$$k \cos^{-1}\left(\frac{R(1 + r_{12}^2 r_{23}^2 e^{-2\alpha L}) - (r_{12}^2 + r_{23}^2 e^{-2\alpha L})}{2(1 - R) r_{12}r_{23}e^{-\alpha L}}\right) + 2\pi m$$

Simplifying further, one obtains $$t = \frac{\lambda}{4\pi n_2 \cos\theta_2} \cdot \left[ k\cos^{-1}\left( \frac{R(1 + r_{12}^2 r_{23}^2 e^{-2\alpha L}) - (r_{12}^2 + r_{23}^2 e^{-2\alpha L})}{2(1-R)r_{12}r_{23}e^{-\alpha L}} \right) + 2\pi m \right] \quad (8)$$

The path length L also depends upon thickness t so that Eq. (8) might have to be implicitly solved for the thickness variable t. Currently, the wavelengths used in the measurement are in the non-absorbing region of the material so that absorption is substantially zero ($e^{-\alpha L}=1$). Therefore, the working equation for the thickness measurement becomes $$t = \frac{\lambda}{4\pi n_2 \cos\theta_2} \left[ k\cos^{-1}\left( \frac{R(1 + r_{12}^2 r_{23}^2) - (r_{12}^2 + r_{23}^2)}{2(1-R)r_{12}r_{23}} \right) + 2\pi m \right] \quad (9)$$

Equation (8) allows the flexibility of doing measurement of thickness in the absorbing region of wavelength as well.

The number of wavelengths required to measure thickness accurately will depend on the working range of the thickness t. One must be able to represent thickness within the specified range with reflectance numbers R that are distinct from each other. For a small thickness range such as $0 < t < 1.2$ micron ($\mu$m), two wavelengths will usually suffice. But for a working range of thickness greater than 1.2 $\mu$m, such as 0.4 $\mu$m $\leq t \leq$ 2.6 $\mu$m, three wavelengths are often necessary to calculate thickness uniquely.

From Eq. (4) with $\alpha = 0$ it is clear that the reflectivity, written as $R(\lambda; t)$ here, is periodic in $\beta$ with period $2\pi$. From Eq. (3) one verifies that for two different choices $\lambda = \lambda_1$ and $\lambda = \lambda_2$ of wavelength and fixed angle $\theta_2$, the reflectivity pair $(R(\lambda_1; t), R(\lambda_2; t))$ will return precisely to its initial value $(R(\lambda_1; t=0), R(\lambda_2; t=0))$ only for values of thickness t for which both conditions $$\frac{\beta_1}{2\pi} = \frac{2n_2(\lambda_1)}{\lambda_1} t\cos\theta_2 = \text{positive integer } M \quad (10)$$

$$\frac{\beta_2}{2\pi} = \frac{2n_2(\lambda_2)}{\lambda_2} t\cos\theta_2 = \text{positive integer } N$$

are satisfied. If, say, four-place accuracy in the measurement of $n_2(\lambda_1)/\lambda_1$, $n_2(\lambda_2)/\lambda_2$, $R(\lambda_1; t)$ and $R(\lambda_2; t)$ and determination of t is imposed, then unless $\lambda_2 n_2(\lambda_1)/\lambda_1 n_2(\lambda_2)$ is a ratio of two small numbers the smallest value of thickness t for which the two conditions (10) are simultaneously satisfied is likely to be of the order of $10^4$ $\mu$m = 1 cm; in this instance, measurement of R at two wavelengths will suffice over an enormous thickness range, of the order of $10^4$ $\mu$m. In practice, it may be difficult to measure $R(\lambda;t)$ accurately to more than two decimal places or to verify the value of $n_2(\lambda)/\lambda$ to more than two decimal places; and one or more values of t hundreds of times smaller than $10^4$ $\mu$m will simultaneously satisfy the conditions (10), within the level of accuracy available.

For example, for a particular photoresist material $$\frac{n_2(\lambda)}{\lambda} = 3.00 \pm .01(\mu m)^{-1} \quad (\lambda = 0.55 \ \mu m)$$

$$= 2.50 \pm .01(\mu m)^{-1} \quad (\lambda = 0.65 \ \mu m)$$

and the conditions (10) become $$\frac{\beta_1}{2\pi} = (5 \pm .02)\cos\theta_2 t = M,$$

$$\frac{\beta_2}{2\pi} = (6 \pm .02)\cos\theta_2 t = N,$$

and these equations are simultaneously satisfied for a choice $$t\cos\theta_2 = 1 \ \mu m;$$

for a range of thickness $t_1 \leq t \leq t_2$ for which $t_2 - t_1 > \sec\theta_2$ ($\mu$m), it is necessary to use more than two wavelengths to insure a unique set of reflectivity numbers $(R(\lambda_1; t), R(\lambda_2; t), \ldots R(\lambda_w; t))$ that in turn specify a unique thickness. More generally, for a thickness range $t_1 \leq t \leq t_2$ one should use a set of different wavelengths $\lambda_1, \lambda_2, \ldots \lambda_w$ for which the simultaneous equations $$\frac{\beta_j}{2\pi} = \frac{2n_2(\lambda_j)}{\lambda_j} t\cos\theta_2 = \quad (11)$$

$$M_j \text{ (positive integer) } (j = 1, 2, \ldots, w)$$

have no thickness solution $t \leq (t_2 - t_1)$. As the thickness range $t_2 - t_1$ grows the required number of different wavelengths will also increase, for fixed $\lambda_j$ ($j=1, 2, \ldots, w$).

After the number of wavelengths required has been determined, the refractive indices $n_1(\lambda)$, $n_2(\lambda)$, $n_3(\lambda)$ for each wavelength are determined and Eq. (9) is substituted with the appropriate values and yields $w (\geq 2)$ thickness equations, one for each wavelength. Several other approaches, using defining equations analogous to Eqs (3'), (9) and (12), may be used to invert Eq. (5) (with $\alpha = 0$); such approaches are recorded as equivalent to the approach adopted in Eqs. (3'), (9) and (12).

The following numerical example serves to illustrate the method for $w = 2$ wavelengths.

| wavelength ($\mu$m) | $\lambda =$ | 0.55 | 0.65 |
|---|---|---|---|
| photoresist refractive index | $n_2 =$ | 1.6401 | 1.6269 |
| silicon refractive index | $n_3 =$ | 4.09 | 3.85 |

This yields the following equations.

$$\lambda = 0.55 \ \mu m: \ t = \quad (12a)$$

$$0.0267 \left[ k\cos^{-1}\left( \frac{1.0107R - 0.24158}{0.20732(1-R)} \right) + 6.2832 \ m \right]$$

$$\lambda = 0.65 \ \mu m: \ t = \quad (12b)$$

$$0.0318 \left[ k\cos^{-1}\left( \frac{1.00938R - 0.22171}{0.19373(1-R)} \right) + 6.2832 \ m \right]$$

As noted above, the reflectivity $R(\theta_1; \lambda; t)$ in Eq. (1) is periodic in $\beta$ with period $2\pi$, with $$\frac{\beta}{2\pi} = \frac{2n_2(\lambda)}{\lambda} t \cos\theta_2 \qquad (3')$$

For two or more different choices of wavelength $\lambda$ for a given material, the values of the ratio $n_2(\lambda)/\lambda$ will probably differ substantially from one another; and this difference will be reflected in the number of full and partial cycles $\cos \beta$ executes as t increases from its minimum value to its maximum value. Letting [x] denote the integral part of the real number x, which is the largest integer less than or equal to x, one verifies from Eqs. (9) and (3') that the integers m and k appearing in Eq. (9) (hereafter referred to as a Permitted Pair of integers) are expressible as $$m = [0.5 + \beta/2\pi] = \left[0.5 + \frac{2n_2(\lambda)}{\lambda} t \cos\theta_2\right], \qquad (13)$$

$$k = (-1)^{[\beta/\pi]} \qquad (14)$$

For a given wavelength $\lambda$, the Permitted Pair (k, m) will range over a finite and predictable set of values for any given thickness range of t. For two (or more) different wavelengths $\lambda_1$ and $\lambda_2$, if $n_2(\lambda_1)/\lambda_1 > n_2(\lambda_2)/\lambda_2$, the pair $(k_1, m_1)$ corresponding to wavelength $\lambda_1$ will change more often than the pair $(k_2, m_2)$ as the thickness variable t increases; but the two pairs $(k_1, m_1)$ and $(k_2, m_2)$ will change in a predictable manner relative to one another over a fixed range of the thickness variable t.

TABLE 1

| Entry no. | $\lambda = 0.55$ μm | | $\lambda = 0.65$ μm | |
|---|---|---|---|---|
| | k | m | k | m |
| 1 | 1 | 0 | 1 | 0 |
| 2 | −1 | 1 | 1 | 0 |
| 3 | −1 | 1 | −1 | 1 |
| 4 | 1 | 1 | −1 | 1 |
| 5 | 1 | 1 | 1 | 1 |
| 6 | −1 | 2 | 1 | 1 |
| 7 | −1 | 2 | −1 | 2 |
| 8 | 1 | 2 | −1 | 2 |
| 9 | 1 | 2 | 1 | 2 |
| 10 | −1 | 3 | 1 | 2 |
| 11 | −1 | 3 | −1 | 3 |
| 12 | 1 | 3 | −1 | 3 |
| 13 | −1 | 4 | −1 | 3 |
| 14 | −1 | 4 | 1 | 3 |
| 15 | 1 | 4 | 1 | 3 |
| 16 | 1 | 4 | −1 | 4 |
| 17 | 1 | 5 | −1 | 4 |
| 18 | −1 | 5 | 1 | 4 |
| 19 | 1 | 5 | 1 | 4 |
| 20 | 1 | 5 | −1 | 5 |
| 21 | −1 | 6 | −1 | 5 |
| 22 | −1 | 6 | 1 | 5 |
| 23 | 1 | 6 | 1 | 5 |
| 24 | −1 | 7 | 1 | 5 |
| 25 | −1 | 7 | −1 | 6 |
| 26 | 1 | 7 | −1 | 6 |
| 27 | 1 | 7 | 1 | 6 |

Table 1 illustrates the relationship of two Permitted Pairs $(k_1, m_1)$ and $(k_2, m_2)$ for the two wavelengths $\lambda_1 = 0.55$ μm and $\lambda_2 = 0.65$ μm and the corresponding photoresist refractive indices $n_2(\lambda)$ given above, for thickness range $0.001$ μm $\leq t \leq 1.200$ μm, with $\cos \theta_2 = 1$. The controlling ratios are $$\frac{n_2(\lambda_1)}{\lambda_1} = 2.982 \ (\mu m)^{-1}$$

$$\frac{n_2(\lambda_2)}{\lambda_2} = 2.503 \ (\mu m)^{-1}$$

so that the Permitted Pair $(k_1, m_1)$ will change more quickly than the Permitted Pair $(k_2, m_2)$ as t increases over its fixed range, viz.

$$.005964 \leq \frac{\beta_1}{2\pi} \leq 7.1568 \ (m_1 = 0,1,2,\ldots,7),$$

$$.005006 \leq \frac{\beta_2}{2\pi} \leq 6.0072 \ (m_2 = 0,1,2,\ldots,6).$$

For this example, as t ranges from 0.99801 to 1.098692, $(k_2, m_2) = (+1,5)$ while the pair $(k_1, m_1)$ assumes the values $(-1,6)$, $(+1,6)$, $(-1,7)$; and as t ranges from 1.098693 to 1.198561 $(k_2, m_2) = (-1,6)$ while the pair $(k_1, m_1)$ assumes the values $(-1,7)$, $(+1,7)$. Table 1 lists the only Permitted Pairs (k, m) that correspond to one another for the two choices of wavelength set forth above and for the given thickness range. For each material $(n_2)$, thickness range, or choice of two or more wavelengths a new table analogous to Table 1 must be generated.

Figure 2:
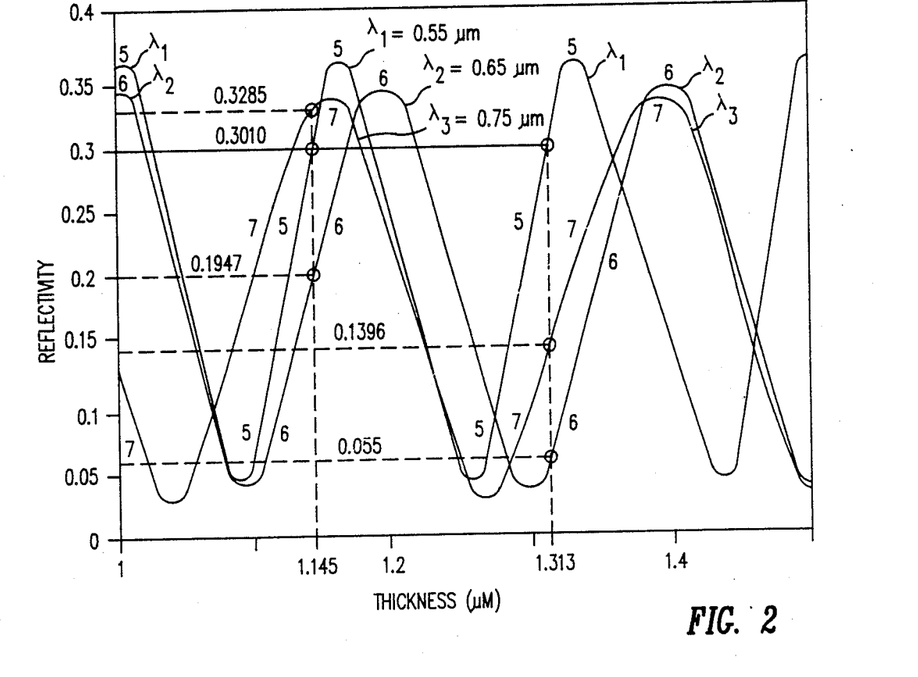
FIG. 2 is a graphic view of reflectivity at normal incidence of a representative film material such as a photo-resist compound, for three different illumination wavelengths λ, as a function of film thickness.

For the above numerical example with two wavelengths, Table 1 contains 27 entries; these can be generated by, for example, determining the Permitted Pairs (k, m) for an array of thicknesses $t = 0.001n(n = 1,2,\ldots, 1200)$ and use of Eqs. (13) and (14) for each wavelength. Hereafter, the array of pairs (k, m) that are generated by Eqs. (13) and (14) for a fixed wavelength $\lambda$ as the thickness variable t is varied over its predetermined thickness range will be called the Permitted Set Of Pairs for that wavelength and thickness range. Eqs. (12a) and (12b) are now used for thickness determination of an actual sample. Consider a measurement of two reflectivity values $R = 0.301$ and $R = 0.1947$ as illustrated in FIG. 2 for the wavelengths $\lambda_1 = 0.55$ μm and $\lambda_2 = 0.65$ μm, respectively. The measured R values are used in Eqs. (12a) and (12b) with the different Permitted Pairs (k, m); and in theory the thickness numbers may be compared to determined an exact match (a single thickness) of the two wavelengths. In practice, noise and precision errors in the measurements interfere here, and coincidence of the thickness numbers thus determined is unlikely.

To compensate for this discrepancy, the following criterion may be used to determine film thickness. The statistical mean $\mu_t$ and standard deviation $\sigma_t$ for each pair of thickness numbers $t_1$ and $t_2$ in each row in Table 1 is calculated according to $$\mu_t = \tfrac{1}{2}(t_1 + t_2)$$

$$\sigma_t = [\tfrac{1}{4}(t_1 - t_2)^2]^{\frac{1}{2}};$$

and the average $\mu_t$ that corresponds to the minimum standard deviation $\sigma_t$ among all rows in Table 1 becomes the designated film thickness. For this first example, this approach produces the following Table 2.

TABLE 2

| Entry no. | $t(\lambda = 0.55$ μm) | $t(\lambda = 0.65$ μm) | Mean | Std. Dev. |
|---|---|---|---|---|
| 1 | 0.00265 | 0.03509 | 0.01887 | 0.01622 |
| 2 | 0.16416 | 0.03509 | 0.09962 | 0.06454 |

TABLE 2-continued

| Entry no. | t(λ = 0.55 μm) | t(λ = 0.65 μm) | Mean | Std. Dev. |
|---|---|---|---|---|
| 3 | 0.16416 | 0.16386 | 0.16401 | 0.00014 |
| 4 | 0.16496 | 0.16386 | 0.16441 | 0.00055 |
| 5 | 0.16496 | 0.23403 | 0.19950 | 0.03454 |
| 6 | 0.33097 | 0.23403 | 0.28250 | 0.04847 |
| 7 | 0.33097 | 0.36281 | 0.34689 | 0.01592 |
| 8 | 0.33267 | 0.36281 | 0.34774 | 0.01507 |
| 9 | 0.33267 | 0.43298 | 0.38287 | 0.05016 |
| 10 | 0.49778 | 0.43298 | 0.46538 | 0.03240 |
| 11 | 0.49778 | 0.56175 | 0.52976 | 0.03199 |
| 12 | 0.50307 | 0.56175 | 0.53241 | 0.02934 |
| 13 | 0.66458 | 0.56175 | 0.61317 | 0.05142 |
| 14 | 0.66458 | 0.63193 | 0.64826 | 0.01633 |
| 15 | 0.66988 | 0.63193 | 0.65091 | 0.01898 |
| 16 | 0.66988 | 0.76070 | 0.71529 | 0.04541 |
| 17 | 0.83139 | 0.76070 | 0.79605 | 0.03535 |
| 18 | 0.83139 | 0.83088 | 0.83113 | 0.00026 |
| 19 | 0.83669 | 0.83088 | 0.83378 | 0.00292 |
| 20 | 0.83669 | 0.95965 | 0.89817 | 0.06148 |
| 21 | 0.99820 | 0.95965 | 0.97892 | 0.01927 |
| 22 | 0.99820 | 1.02982 | 1.01401 | 0.01582 |
| 23 | 1.00350 | 1.02982 | 1.01666 | 0.01316 |
| 24 | 1.16501 | 1.02982 | 1.09742 | 0.06759 |
| 25 | 1.16501 | 1.15859 | 1.16180 | 0.00321 |
| 26 | 1.17031 | 1.15859 | 1.16445 | 0.00587 |
| 27 | 1.17031 | 1.22877 | 1.19954 | 0.02923 |

For the first exammple, as illustrated in Table 2, the chosen thickness is t=0.16401 μm (Entry No. 3).

For thicknesses t between 0.4 μm and 2.6 μm, this approach often requires use of three wavelengths to determine t sufficiently accurately. The following example serves to illustrate the method for w=3 wavelengths.

| wavelength (μm) | λ = 0.55 | 0.65 | 0.75 |
|---|---|---|---|
| photoresist refractive index | $n_2$ = 1.6401 | 1.6269 | 1.6238 |
| silicon refractive index | $n_3$ = 4.09 | 3.85 | 3.733 |

The following equations are used here.

$$\lambda = 0.55 \ \mu m: t = 0.0267 \left[ k\cos^{-1}\left( \frac{1.01074R - 0.24158}{0.20732(1 - R)} \right) + 6.2832 \ m \right] \quad (15a)$$

$$\lambda = 0.67 \ \mu m: t = 0.0318 \left[ k\cos^{-1}\left( \frac{1.00938R - 0.22171}{0.19373(1 - R)} \right) + 6.2832 \ m \right] \quad (15b)$$

$$\lambda = 0.75 \ \mu m: t = 0.0367 \left[ k\cos^{-1}\left( \frac{1.00876R - 0.21155}{0.18722(1 - R)} \right) + 6.2832 \ m \right] \quad (15c)$$

For each equation, a Permitted Pair (k, m) is determined for each thickness between 0.4 and 2.6 microns at increments of 0.001 μm or using any other desired array of thicknesses t. The R values are precalculated, using Eq. (1) as before with the appropriate values of t. The Permitted Pairs (k, m) for the three wavelengths for the same thickness are combined to form one row in Table 3, with repeating entries discarded as before. Table 3 for the 0.4 to 2.6 μm thickness range has 69 entries. As a comparison, using 5 wavelengths with the same range an analogous table contains about 115 entries.

TABLE 3

| Entry no. | λ = 0.55 μm k | m | λ = 0.65 μm k | m | λ = 0.75 μm k | m | Entry no. | λ = 0.55 μm k | m | λ = 0.65 μm k | m | λ = 0.75 μm k | m |
|---|---|---|---|---|---|---|---|---|---|---|---|---|---|
| 1 | 1 | 2 | 1 | 2 | −1 | 2 | 36 | 1 | 10 | −1 | 8 | −1 | 7 |
| 2 | −1 | 3 | 1 | 2 | −1 | 2 | 37 | −1 | 10 | −1 | 8 | −1 | 7 |
| 3 | −1 | 3 | 1 | 2 | 1 | 2 | 38 | −1 | 10 | 1 | 8 | −1 | 7 |
| 4 | −1 | 3 | −1 | 3 | 1 | 2 | 39 | −1 | 10 | 1 | 8 | 1 | 7 |
| 5 | 1 | 3 | −1 | 3 | 1 | 2 | 40 | 1 | 10 | 1 | 8 | 1 | 7 |
| 6 | 1 | 3 | −1 | 3 | −1 | 3 | 41 | 1 | 10 | −1 | 9 | 1 | 7 |
| 7 | −1 | 4 | −1 | 3 | −1 | 3 | 42 | 1 | 10 | −1 | 9 | −1 | 8 |
| 8 | −1 | 4 | 1 | 3 | −1 | 3 | 43 | −1 | 11 | −1 | 9 | −1 | 8 |
| 9 | 1 | 4 | 1 | 3 | −1 | 3 | 44 | −1 | 11 | 1 | 9 | −1 | 8 |
| 10 | 1 | 4 | 1 | 3 | 1 | 3 | 45 | 1 | 11 | 1 | 9 | −1 | 8 |
| 11 | 1 | 4 | −1 | 4 | 1 | 3 | 46 | 1 | 11 | 1 | 9 | 1 | 8 |
| 12 | −1 | 5 | −1 | 4 | 1 | 3 | 47 | 1 | 11 | −1 | 10 | 1 | 8 |
| 13 | −1 | 5 | 1 | 4 | 1 | 3 | 48 | −1 | 12 | −1 | 10 | 1 | 8 |
| 14 | −1 | 5 | 1 | 4 | −1 | 4 | 49 | −1 | 12 | −1 | 10 | −1 | 9 |
| 15 | 1 | 5 | 1 | 4 | −1 | 4 | 50 | −1 | 12 | 1 | 10 | −1 | 9 |
| 16 | 1 | 5 | −1 | 5 | −1 | 4 | 51 | 1 | 12 | 1 | 10 | −1 | 9 |
| 17 | −1 | 6 | −1 | 5 | −1 | 4 | 52 | 1 | 12 | 1 | 10 | 1 | 9 |
| 18 | −1 | 6 | −1 | 5 | 1 | 4 | 53 | −1 | 13 | 1 | 10 | 1 | 9 |
| 19 | −1 | 6 | 1 | 5 | 1 | 4 | 54 | −1 | 13 | −1 | 11 | 1 | 9 |
| 20 | 1 | 6 | 1 | 5 | 1 | 4 | 55 | 1 | 13 | −1 | 11 | 1 | 9 |
| 21 | 1 | 6 | 1 | 5 | −1 | 5 | 56 | 1 | 13 | −1 | 11 | −1 | 10 |
| 22 | −1 | 7 | 1 | 5 | −1 | 5 | 57 | 1 | 13 | 1 | 11 | −1 | 10 |
| 23 | −1 | 7 | −1 | 6 | −1 | 5 | 58 | −1 | 14 | 1 | 11 | −1 | 10 |
| 24 | −1 | 7 | −1 | 6 | 1 | 5 | 59 | −1 | 14 | −1 | 12 | −1 | 10 |
| 25 | 1 | 7 | −1 | 6 | 1 | 5 | 60 | −1 | 14 | −1 | 12 | 1 | 10 |
| 26 | 1 | 7 | 1 | 6 | 1 | 5 | 61 | 1 | 14 | −1 | 12 | 1 | 10 |
| 27 | −1 | 8 | 1 | 6 | 1 | 5 | 62 | 1 | 14 | 1 | 12 | 1 | 10 |
| 28 | −1 | 8 | 1 | 6 | −1 | 6 | 63 | 1 | 14 | 1 | 12 | −1 | 11 |
| 29 | −1 | 8 | −1 | 7 | −1 | 6 | 64 | −1 | 15 | 1 | 12 | −1 | 11 |
| 30 | 1 | 8 | −1 | 7 | −1 | 6 | 65 | −1 | 15 | −1 | 13 | −1 | 11 |
| 31 | 1 | 8 | −1 | 7 | 1 | 6 | 66 | 1 | 15 | −1 | 13 | −1 | 11 |
| 32 | 1 | 8 | 1 | 7 | 1 | 6 | 67 | 1 | 15 | −1 | 13 | 1 | 11 |
| 33 | −1 | 9 | 1 | 7 | 1 | 6 | 68 | 1 | 15 | 1 | 13 | 1 | 11 |
| 34 | −1 | 9 | −1 | 8 | 1 | 6 | 69 | −1 | 16 | 1 | 13 | 1 | 11 |

TABLE 3-continued

| Entry no. | λ = 0.55 μm k | m | λ = 0.65 μm k | m | λ = 0.75 μm k | m | Entry no. | λ = 0.55 μm k | m | λ = 0.65 μm k | m | λ = 0.75 μm k | m |
|---|---|---|---|---|---|---|---|---|---|---|---|---|---|
| 35 | −1 | 9 | −1 | 8 | −1 | 7 | | | | | | | |

For this second example, the three thickness equations (15a), (15b), (15c) are now used. Consider a measurement of three reflectivity values R=0.3010, 0.1382, 0.1537 for wavelengths λ=0.55, 0.65, 0.75 μm, respectively. For this second example above, the algorithm would produce the following (partial) table results.

TABLE 4

| Entry no. | t(λ = 0.55 μm) | t(λ = 0.65 μm) | t(λ = 0.75 μm) | Mean | Std. Dev. |
|---|---|---|---|---|---|
| 1 | 0.36533 | 0.46584 | 0.39074 | 0.40731 | 0.04267 |
| 2 | 0.47303 | 0.46584 | 0.39074 | 0.44321 | 0.03721 |
| 3 | 0.47303 | 0.46584 | 0.53302 | 0.49063 | 0.03012 |
| 4 | 0.47303 | 0.53299 | 0.53302 | 0.51301 | 0.02827 |
| 5 | 0.53301 | 0.53299 | 0.53302 | 0.53300 | 0.00013 |
| 6 | 0.53301 | 0.53299 | 0.62168 | 0.56256 | 0.04181 |
| 7 | 0.64070 | 0.53299 | 0.62168 | 0.59846 | 0.04694 |
| 8 | 0.64070 | 0.53299 | 0.62168 | 0.64266 | 0.01799 |
| 9 | 0.70068 | 0.66561 | 0.62168 | 0.66266 | 0.03232 |
| 10 | 0.70068 | 0.66561 | 0.76396 | 0.71008 | 0.04070 |
| 11 | 0.70068 | 0.73275 | 0.76396 | 0.73246 | 0.02584 |
| 12 | 0.80838 | 0.73275 | 0.76396 | 0.76836 | 0.03103 |
| 13 | 0.80838 | 0.86538 | 0.76396 | 0.81257 | 0.04151 |
| 14 | 0.80838 | 0.86538 | 0.85262 | 0.84212 | 0.02443 |
| 15 | 0.80835 | 0.86538 | 0.85262 | 0.86212 | 0.00682 |
| 16 | 0.80835 | 0.93252 | 0.85262 | 0.88450 | 0.03456 |
| 17 | 0.97605 | 0.93252 | 0.85262 | 0.92040 | 0.05112 |
| ... | ... | ... | ... | ... | ... |

The thickness determined by this approach is Entry No. 5 with mean thickness t=0.53300 μm, corresponding to the minimum standard deviation of 0.00013. The nearest "competitor" to entry No. 5, with standard deviation 0.00013, is entry No. 15, with standard deviation 0.00682.

More generally, where w(≧2) wavelengths $\lambda_1, \lambda_2, \ldots, \lambda_w$, are used the analog of Tables 1 and 2 will be generated, with the statistical mean μ and standard deviation σ being determined by $$\mu_t = \frac{1}{W} \sum_{j=1}^{W} t(\lambda_j; k_j, m_j) \quad (16)$$

$$\sigma_t = \frac{1}{W} \left[ \sum_{j=2}^{W} \sum_{i=1}^{j-1} (t(\lambda_j; k_i, m_i) - t(\lambda_j; k_j, m_j))^2 \right]^{\frac{1}{2}}, \quad (17)$$

where t($\lambda_j$; $k_j$, $m_j$) is the thickness t at wavelength $\lambda_j$ corresponding to one of the entries (specified by a particular choice of the permitted pairs of integers k=±1 and m=1,2,...) in the analog of Table 2.

An alternative method uses a table look-up approach, with an analogous criterion being applied for the choice of thickness t using two or more wavelengths. As an example, consider the thickness range 0.400 μm≦t≦2.600 μm. With increments of Δt=0.001 μm imposed, the total number of separate thicknesses is 2201.

With this approach adopted, the reflectively values R are computed for each of the chosen wavelengths $\lambda_j = \lambda_1, \lambda_2, \ldots, \lambda_w$ for each value of thickness $t_s$(s=1, 2, ..., M) for the predetermined film/substrate materials and a fixed incidence angle $\theta_1$; this yields an array of reflectivity values R($\theta_1$; $\lambda_j$; $t_s$). Reflectivity measurements at each wavelength $\lambda_j=\lambda_1,\lambda_2, \ldots, \lambda_w$ are now made at the incidence angle $\theta_1$ on the film/substrate combination with unknown thickness t; these yield a sequence of values R'($\theta_1$; $\lambda_1$), R'($\theta_1$; $\lambda_2$), ..., R'($\theta_1$; $\lambda_w$). One then computes the variance $$\chi_R(t_s) = \frac{1}{W} \left[ \sum_{j=1}^{W} (R(\theta_1;\lambda_j;t_s) - R'(\theta_1;\lambda_j))^2 \right]^{\frac{1}{2}} \quad (18)$$

and chooses the "granular" thickness $t_s$ corresponding to minimum variance. It is possible that two or more distinct values of film thickness $t_s$ will produce the same minimum variance, but the probability of this occurrence is quite small; if this does occur, other criteria should be invoked to determine which value of "granular" thickness is preferable. The equidistant array of film thickness $\{t_s\}_{s=1}^M$ may be replaced by any other reasonable array covering the same range of thicknesses (e.g., 0.400 μm≦t≦2.600 μm).

The preceding discussion has assumed that the film refractive index $n_2$ is known and that the film thickness t, inter alia, is unknown. If the situation is reversed and $n_2$ is now the sole independent unknown, several methods are available to estimate the value of $n_2(\lambda)$ of the particular wavelength λ used. Assume one has made a sequence of M(≧) reflectivity measurements $\{R_{meas}^{(i)}\}_{i=1}^M$ with each $R_{meas}^{(i)}$ corresponding to a predetermined combindation ($t_i$, $\theta_{1,i}$, $k_i$) of film thickness $t_i$, incidence angle $\theta_{1,i}$ and polarization index $k_i$(=p or s). The refraction angle $\eta_2$ and index $n_2$ (both unknown) are related by the equation $$\cos \theta_2 = [1 - \sin^{2\theta} 1/n_2^2]^{\frac{1}{2}}, \quad (19)$$

which follows from Eq. (2).

A sequence, preferably monotonically increasing or monotonically decreasing, $\{n_{2,j}\}_{j=1}^N$ of realistic values of the index $n_2$ is chosen and a corresponding sequence $\{\theta_{2,j}\}_{j=1}^N$ of values of the angle θ is determined from Eq. (19). A sequence of values $$R_{ij} = R(\theta_{1,i};\lambda;t_i,k_i;n_2 = n_{2,j};\theta_2 = \theta_{2,j};n_3;\theta_3) \quad (20)$$

$$(i = 1,2,\ldots,M; j = 1,2,\ldots,N)$$

is determined from Eqs. (1), (2), (3) and the corresponding equations for reflection coefficients $r_{12,p}, r_{23,p}, r_{12,s}$ and $r_{12,s}$. A sequence $\{S_j\}_{j=1}^n$ of terms with $$S_j = \sum_{i=1}^{M} |R_{meas}^{(i)} - R_{ij}|^h \quad (21)$$

is formed where h is a predetermined positive real number, and the minimum value for $S_j$, said for j=J, is determined. The value $n_2=n_{2,J}$ is then chosen as the refractive index of the film. This method can be applied for a single measured value of reflectivity, with M=1 as noted above.

It may occur that more than one value, said j=$J_1$ and j=$J_2$ of the sequence $\{S_j\}$ produces substantially the same minimum value. If $J_2 = J_1 \pm 1$, these two values are consecutive and one might choose $$n_2 = \frac{1}{2}(n_{2,J_1} + n_{2,J_2})$$

as the unknown refractive index. If the two values $J_1$ and $J_2$ are not consecutive so that $n_{2,J_1}$ and $n_{2,J_2}$ differ substantially, one may invoke additional physical considerations (e.g., narrow the realistic and expected range of $n_2$) so that all but one of the values $n_{2,J}$ corresponding to minimum $S_j$ are eliminated.

A second method assumes that a sequence $\{R_{meas}^{(i)}\}_{i=1}^{M}$ of measurements of reflectivity R have been made for a corresponding sequence $\{t_i\}_{i=1}^{M}$ of known thicknesses ($M \geq 1$). Assume one has made an initial choice $n_2 = n_{2,0}$ of refractive index for the film and form the sum $$S = \sum_{i=1}^{M} |R_{meas}^{(i)} - R(\theta_1; \lambda; t_i; n_2; n_3)|^2 = \sum_{i=1}^{M} f_i(n_2)^2 \qquad (22)$$

where $R(\theta_1; \lambda, t_i, n_2; n_3)$ is the reflectivity calculated from Eq. (1) with $$\cos\theta_2 = |1 - \sin^2\theta 1/n_2^2|^{\frac{1}{2}},$$

$$\cos\theta_3 = |1 - \sin^2\phi 1/n_3^2|^{\frac{1}{2}},$$

and the reflection coefficients $r_{12}$ and $r_{23}$ are determined as shown there for the corresponding choice of p-polarization or s-polarization light used in the measurement of R. Ideally, the (realistic) choice $n_2 = n_{2,0}$ is the refractive index value that minimizes S, write $$f_i(n_2) = f_i(\hat{n}_2 + \Delta n_2) = f_i(\hat{n}_2) + \left(\frac{\partial f_i}{\partial n_2}\right)_{\hat{n}_2} \Delta n_2 + \qquad (23)$$

$$\frac{1}{2}\left(\frac{\partial^2 f_i}{\partial n_2^2}\right)_{\hat{n}_2}(\Delta n_2)^2 + O((\Delta n_2)^2),$$

$$\Delta n_2 = n_{2,o} - \hat{n}_2,$$

where $o((\Delta n_2)^2)$ denotes a function $B(\Delta n_2)$ that satisfies $\lim_{\Delta n_2 \to 0} B((\Delta n_2)/((\Delta n_2)^2) = 0$. Only the terms that are constant, linear or quadratic in $\Delta n_2$ are considered further here. The sum S then becomes $$S = \sum_{i=1}^{M} \left| f_i(\hat{n}_2)^2 + 2\left(f_i \frac{\partial f_i}{\partial n_2}\right)_{\hat{n}_2} \Delta n_2 + \left(f_i \frac{\partial^2 f_i}{\partial n_2^2} + \left(\frac{\partial f_i}{\partial n_2}\right)^2\right)_{\hat{n}_2} (\Delta n_2)^2 \right|,$$

and S is (approximately) minimized for the choice $$\Delta n_2 = -\sum_{i=1}^{M} \left(f \frac{\partial f_i}{\partial n_2}\right)_{\hat{n}_2} / \sum_{j=1}^{M} \left(f_j \frac{\partial^2 f_j}{\partial n_2^2} + \left(\frac{\partial f_j}{\partial n_2}\right)^2\right)_{\hat{n}_2}. \qquad (24)$$

In practice, one does not know the value $\hat{n}_2$ at which $f_i$ and its first two derivatives are evaluated and these functions are evaluated at $n_2 = n_{2,o}$ instead. This motivates the use of an iterative procedure that generates a sequence $\{n_{2,i}\}_i$ of approximations that, one anticipates, will converge to the value $\hat{n}_2$. Assume that one has produced the subsequence $\{n_{2,i}\}_{i=0}^{I}$ of approximations. The next approximation $n_{2,I+1}$ is determined by $$n_{2,I+1} = n_{2,I} - \qquad (25)$$

$$\left. \sum_{i=1}^{M} \left(f_i \frac{\partial f_i}{\partial n_2}\right)_{n_{2,I}} \middle/ \sum_{j=1}^{M} \left(f_j \frac{\partial^2 f_j}{\partial n_2^2} + \left(\frac{\partial f_j}{\partial n_2}\right)^2\right)_{n_{2,I}} \right. =$$

$$n_{2,I} - \Delta_I$$

This determines the approximation sequence, and with mild restrictions imposed on the functions $f_i$ one is guaranteed that this sequence will converge to a limit that produces a local minimum for S. One can truncate the sequence and terminate the iteration procedure where $$|n_{2,I+1} - n_{2,I}| = |\Delta_I| < \epsilon, \qquad (26)$$

where $\epsilon$ is a small, positive predetermined number such as $10^{-5}$. To promote monotone convergence of the sequence $\{n_{2,I}\}$ to $\hat{n}$ and suppress oscillation, one may replace Eq. (22) by $$n_{2,I+1} = n_{2,I} - \Delta_I / \eta (\eta \geq 1) \qquad (27)$$

with $\eta$ a predetermined number.

Table 5 presents the results of a computation of the refractive index $n_2$ of an AZ photoresist film of four different film thicknesses t (in $\mu$m) = 1.661, 0.997, 1.324 and 1.997, where the films are mounted on a Si substrate of thickness $\sim 10$ $\mu$m. Reflectivity $R_{meas}$ is determined for each of the four film thicknesses at each of three wavelengths $\lambda = 0.55$ $\mu$m, 0.65 $\mu$m and 0.75 $\mu$m for a p-polarized beam at incidence angle $\theta_1 = 0°$. The corresponding (known) refractive indices $n_3(\lambda)$ of the substrate are shown in Table 5, and the iteration results for an initial choice $n_{2,o} < \hat{n}_2$ and an initial choice $n_{2,o} > \hat{n}_2$ are shown for each wavelength $\lambda$ with the choice $\eta = 2$ in Eq. (27). Note that the sequence $\{n_{2,i}\}$ converges monotanically to $\hat{n}_2$ (to within one part in $10^5$) within about ten iterations; each such set of iterations requires about 250 milliseconds with a microcomputer program.

TABLE 5

| Wavelength | $\lambda = 0.55$ $\mu$m | $\lambda = -0.65$ $\mu$m | $\lambda = 0.75$ $\mu$m |
|---|---|---|---|
| $n_3(\lambda)$ | 4.09 | 3.85 | 3.733 |
| $\theta_1$ | 0° | 0° | 0° |
| $R_{meas}^{(1)}$ | 0.3382 | 0.0991 | 0.1939 |
| $R_{meas}^{(2)}$ | 0.3523 | 0.3453 | 0.1178 |
| $R_{meas}^{(3)}$ | 0.3517 | 0.1479 | 0.2356 |
| $R_{meas}^{(4)}$ | 0.3272 | 0.3453 | 0.1008 |
| $t_1 = 1.661$ $\mu$m, $t_2 = 0.997$ $\mu$m, $t_3 = 1.324$ $\mu$m, $t_4 = 1.977$ $\mu$m | | | |
| $n_{2,0}$ | 1.6300 | 1.6200 | 1.6200 |
| $n_{2,1}$ | 1.6373 | 1.6287 | 1.6402 |
| $n_{2,2}$ | 1.6411 | 1.6334 | 1.6391 |
| $n_{2,3}$ | 1.6435 | 1.6363 | 1.6386 |
| $n_{2,4}$ | 1.6459 | 1.6388 | 1.6382 |
| $n_{2,5}$ | 1.6459 | 1.6388 | 1.6382 |
| $n_{2,6}$ | 1.6565 | 1.6393 | 1.6381 |
| $n_{2,7}$ | 1.6467 | 1.6395 | 1.6380 |
| $n_{2,8}$ | 1.6469 | 1.6397 | 1.6380 |
| $n_{2,9}$ | 1.6470 | 1.6398 | 1.6380 |
| $n_{2,10}$ | 1.6470 | 1.6398 | 1.6380 |
| $\hat{n}_2$(est.) | 1.6470 | 1.6398 | 1.6380 |
| $n_{2,0}$ | 1.6500 | 1.6700 | 1.6700 |
| $n_{2,1}$ | 1.6480 | 1.6592 | 1.6319 |
| $n_{2,2}$ | 1.6475 | 1.6498 | 1.6359 |
| $n_{2,3}$ | 1.6473 | 1.6441 | 1.6368 |

TABLE 5-continued

| Wavelength | $\lambda = 0.55\ \mu m$ | $\lambda = -0.65\ \mu m$ | $\lambda = 0.75\ \mu m$ |
|---|---|---|---|
| $n_{2,4}$ | 1.6471 | 1.6418 | 1.6374 |
| $n_{2,5}$ | 1.5461 | 1.6403 | 1.6379 |
| $n_{2,6}$ | 1.6471 | 1.6400 | 1.6379 |
| $n_{2,7}$ | 1.6471 | 1.6399 | 1.6380 |
| $n_{2,8}$ | 1.6470 | 1.6393 | 1.6380 |
| $n_{2,9}$ | 1.6470 | 1.6398 | 1.6380 |
| $n_{2,10}$ | 1.6470 | 1.6398 | 1.6380 |
| $\hat{n}_2$(est.) | 1.6470 | 1.6398 | 1.6380 |

If the values $R_{meas}$ are all close to the maximum value or all close to the minimum value of $R_{meas}$ indicated by the theoretical expression in Eq. (1), several adjacent solutions $\hat{n}_2$ may exist for a given $\lambda$, and the acceptable range of $n_2$ may have to be severely restricted from other physical considerations in order to provide a unique solutions $\hat{n}_2$ within this range. One method of insuring that the values $R_{meas}$ are separated sufficiently so that this does not occur is to vary the incidence angle $\theta_1$ for each measurement.

A third method, which is analogous to the second method, rewrites Eqs. (23) and (22), respectively, in the form $$f(\hat{n}_2) = f(n_{20} - \Delta n_2) \quad (28)$$

$$= f(n_{2,0}) - \left(\frac{\partial f_i}{\partial n_2}\right)_{n_{2,0}} \Delta n_2 +$$

$$\tfrac{1}{2}\left(\frac{\partial^2 f_i}{\partial n_2^2}\right)_{n_{2,0}} (\Delta n_2)^2 + o((\Delta n_2)^2)$$

$$S = \sum_{i=1}^{M} (f(n_{2,0} - \Delta n_2))^2 \quad (29)$$

$$\doteq \sum_{i=1}^{M} \left| f(n_{2,0})^2 - 2\left(f_i \frac{\partial f_i}{\partial n_2}\right)_{n_{2,0}} \Delta n_2 + \left(f_i \frac{\partial^2 f_i}{\partial n_2^2} + \left(\frac{\partial f_i}{\partial n_2}\right)^2\right)_{n_{2,0}} (\Delta n_2)^2 \right|$$

The sum S is substantially zero for the choice $$\Delta n_2 = n_{2,i} - n_{2,i+1} = \left\{ \sum_{j=1}^{M} \left(f_j \frac{\partial f_j}{\partial n_2}\right)_{n_{2,i}} \pm \left[\left(\sum_{j=1}^{M} \left(f_j \frac{\partial f_j}{\partial n_2}\right)_{n_{2,i}}\right)^2 - \left(\sum_{j=1}^{M} f(n_2)_{n_{2,i}}\right)^2 \left(\sum_{k=1}^{M} \left(f_k \frac{\partial^2 f_k}{\partial n_2^2} + \left(\frac{\partial f_k}{\partial n_2}\right)^2\right)_{n_{2,i}}\right)\right]^{\tfrac{1}{2}} \right\} / \quad (30)$$

$$\sum_{j=1}^{M} \left[\left(f_j \frac{\partial^2 f_j}{\partial n_2^2}\right)_{n_{2,i}} + \left(\frac{\partial f_j}{\partial n_2}\right)^2_{n_{2,i}}\right] = \Delta_i\ (i = 0, 1, 2, \ldots).$$

One then follows the iteration procedure $$n_{2,i+1} = n_{2,i} - \Delta_i/\eta(\eta \geq 1) \quad (31)$$

and determines a cutoff on iteration by Eq. (29) as usual. If only a single measurement is used (M=1), Eq. (30) simplifies to $$\Delta_i = f(n_{2,i})\left\{ \frac{\partial f}{\partial n_2} \pm \left[-\beta \frac{\partial^2 f}{\partial n_2^2}\right]^{\tfrac{1}{2}} \right\}_{n_{2,i}} / \quad (32)$$

$$\left[f \frac{\partial^2 f}{\partial n_2^2} + \left(\frac{\partial f}{\partial n_2}\right)^2\right]_{n_{2,i}}$$

and if $f(n_{2,i})\doteq 0$ so that the second term in the numerator can be dropped, Eq. (32) resembles Eq. (24) in form.

A fourth method, which is formally *exact*, to determine $n_2$ uses only s-polarization electromagnetic radiation to illuminate the film substrate combination and for the measurement of reflectivity R (denoted $R_s$ here to emphasize the particular choice of s-polarization). The reflectivity coefficients may be written (for $n_1 = 1$ here)

$$r_{12,s} = \frac{1-z}{z+1},$$

$$r_{23,s} = \frac{\psi_{13}z - 1}{1 + \psi_{13}z},$$

$$z = [n_2^2 - \sin^2\theta_1]^{\tfrac{1}{2}}/\cos\theta_1\ (z > 1\ \text{for}\ n_2 > 1), \quad (33)$$

$$1/\psi_{13} = \cos\theta_1/n_3\cos\theta_3 = \cos\theta_1/[n_3^2 - \sin^2\theta_1]^{\tfrac{1}{2}}\ (<1), \quad (34)$$

and Eq. (1) may be rewritten in the form $$(Z^2)^2(1 - \cos\phi Z)\psi_{13}^2 - Z^2[(1 + \psi_{13}^2)(1 + \cos\phi Z) - \quad (35)$$

$$4\psi_{13}/x] + (1 - \cos\phi z) = F(z) = 0,$$

$$\phi = 4\pi t \cos\theta_1/\lambda,$$

$$x = (1 - R_s)/(1 + R_s)/(x < 1).$$

Equation (35) has one formal solution $z=0$ ($n_2 = \sin\theta_1$), which is not realistic. If this is treated formally as a quadratic in $z^2$, $$F(z) = \psi_{13}^2 A(z)(z^2) - 2B(z)z^2 + A(z) = 0 \quad (36)$$

$$\frac{dF}{dz} = \psi_{13}^2 \frac{dA}{dz}z^4 + 4\psi_{13}^2 A(z)z^3 - \quad (37)$$

$$2\frac{dB}{dz}z^2 - 4B(z)z + \frac{dA}{dz}.$$

$$B(Z) = (1 + \psi_{13}^2)(1 + \cos\phi Z) - 4\psi_{13}/x.$$

The quantity A(z) is non-negative for all z, and the quantity B(z) is non-negative for all z if $$\psi_{13} \geq \{2/x - [(2/x)^2 - (1 + \cos\phi Z)^2]\}/(1 + \cos\phi Z),$$

which is assumed here. The formal solution of Eq. (36) is $$Z^2 = f_\pm(Z;\psi_{13}) = \quad (39)$$

-continued
$$\frac{1}{\psi_{13}^2 A(Z)} \{B(Z) \pm [B(Z)^2 - \psi_{13}^2 A(Z)^2]^{\frac{1}{2}}\}.$$

At $\phi z = 2n\pi$ ($n=0,1,2,\ldots$) $f_+(z;\psi_{13})$ is formally infinite and $f_-(z;\psi_{13})$ is formally zero (both physically unrealistic) and both "roots" $f_\pm(z;\psi_{13})$ are non-negative for all z. As $\phi z$ increases from $2n\pi$ toward $(2n+1)\pi$ the two "roots $f_\pm(z;\psi_{13})$ approach one another. From further analysis it appears that Eq. (36) has at least one positive root in each internal ($2n\pi$, $(2n+1)\pi$). Knowing this, one can use an iterative technique such as the Newton method (discussed in S. Borotsky, *Elementary Theory of Equations*, 1950, The MacMillon Company, pp. 109-112) to obtain a sequence of approximations for a solution $z^2$ of Eq. (36) in the open intervals $(0,\pi)$, $(\pi,3\pi)$, ... $((2n-1)\pi, (2n+1)\pi)$, .... The Newton method, as used here, begins with an initial estimate such as $z_0 = \pi/2$ in the interval $(0,\pi)$ or $z_0 = (2n\pm\frac{1}{2})\pi$ in the interval $((2n-1)\pi, (2n+1)\pi)$ and generates a sequence of approximations $\{z_m\}_m$ according to $$z_m = z_{m-1} - \frac{F(z_{m-1})}{\left(\frac{dF}{dz}\right)_{z_{m-1}}} \quad (m=1,2,3,\ldots) \quad (40)$$

One terminates the sequence at, say, $m=M$ when $|z_m - z_{m-1}| < E$ for $m \geq M$, where E is a small predetermined positive number such as $10^{-5}$. Any suitable iterative method may be used to obtain solutions of Eq. (36). The desired solution $n_2$ for the refractive index is then determined from the relation $$n_2 = [(\hat{z}\cos\theta_1)^2 + \sin^2\theta_1]^{\frac{1}{2}} \quad (41)$$

where $\hat{z}$ is the estimate determined from the above iterative method.

At most only one estimate $\hat{z}$ determined above will be physically realistic for the particular film and wavelength used. Thus, one might focus on the solution or solutions z in a particular interval $(2n-1)\pi$, $(2n+1)\pi)$ that contains the predetermined range of physically realistic values of z.

Although the preferred embodiments of the invention have been shown and described herein, variation and modification may be made without departing from what is regarded as the scope of the invention.

We claim:

1. A method for determining the unknown thickness t, within a predetermined thickness range $t_{min} \leq t \leq t_{max}$, of a film of material with predetermined indices of refraction $n_2 = n_2(\lambda_j)$ ($j=1,2,\ldots,w$) at a plurality of $w(\geq 2)$ distinct wavelengths $\lambda = \lambda_1, \lambda_2, \ldots, \lambda_w$ of light used to illuminate the film, where the film material is at least partially transparent to light at each of these wavelengths, where the film is attached on one of its faces to a solid substrate of predetermined material having predetermined indices of refraction $n_3 = n_3(\lambda_j)$ at the plurality of wavelengths $\lambda_j = \lambda_1, \lambda_2, \ldots, \lambda_w$, where the coefficient of amplitude reflection, for a light beam of polarization index $k'(=p,s)$, incidence angle $\theta_1'$ and transmission angle $\theta_2'$ of a light beam of wavelength $\lambda_j$ ($j=1,2,\ldots,w$) traveling in a vacuum toward the interface between the vacuum and the film, is a predetermined number $r_{12} = r_{12,k'}(\theta_1', \theta_2'; \lambda_j)$ for each of the wavelengths $\lambda_j$, and where the coefficient of amplitude reflection, for a light beam of polarization index $k'(=p, s)$, incidence angle $\theta_2'$ and transmission angle $\theta_3'$ of a light beam of wavelength $\lambda_j$ traveling in the film material toward the interface between the film and the substrate, is a predetermined number $r_{23}r_{23,k}(\theta_2', \theta_3'; \lambda_j)$, the method comprising the steps of:

directing a beam of light of polarization index $k(=p, s)$ at each of the wavelengths $\lambda_1, \lambda_2, \ldots, \lambda_w$ at a predetermined, nonnegative incidence angle $\theta_1$ at the exposed face of the film within a vacuum or air;

measuring the reflectivities $R_j = R(\theta_1; \lambda_j)$ ($j=1,2,\ldots,w$) of the light beam intensity at the exposed face of the film at incidence angle $\theta_1$ and at each of the respective wavelengths $\lambda_1, \lambda_2, \ldots, \lambda_w$;

for each reflectivity number $R_j$ determining a thickness $t(\lambda_j)$ by inverting the equation $$\cos\left(\frac{4\pi n_2(\lambda_j)}{\lambda_j} t(\lambda_j)\cos\theta_2\right) = \frac{R_j(1 + r_{12}^2 r_{23}^2) - r_{12}^2 - r_{23}^2}{2(1-R_j)r_{12}r_{23}},$$

to obtain a sequence of w-tuples of film thickness $\{t_m(\lambda_1), t_m(\lambda_2), \ldots, t_m(\lambda_w)\}_{m=1}^M$ ($M \geq 1$) that are solutions of this equation, with $\cos\theta_2 = (1-\sin^2\theta_1/n_2(\lambda_j)^2)^{\frac{1}{2}}$, $\cos\theta_3 = (1-\sin^2\theta_1/n_3(\lambda_j)^2)^{\frac{1}{2}}$, $r_{12} = r_{12,k}(\theta_1, \theta_2; \lambda_j)$, $r_{23} = r_{23,k}(\theta_2, \theta_3; \lambda_j)$, for the wavelength $\lambda = \lambda_j$;

for each w-tuple of thicknesses, determining the statistical means $\mu_t$ and standard deviation $\sigma_t$ for that w-tuple; and choosing the thickness w-tuple that produces the smallest standard deviation $\sigma_t$ among a sequence of such w-tuples, and designating the mean $\mu_t$ of that thickness w-tuple as the thickness t of the film.

2. A method according to claim 1, wherein the step of determining said thickness or thicknesses $t(\lambda_j)$ by inverting said equation $$\cos\left(\frac{4\pi n_2(\lambda_j)}{\lambda_j} t(\lambda_j)\cos\theta_2\right) = \frac{R_j(1 + r_{12}^2 r_{23}^2) - r_{12}^2 - r_{23}^2}{2(1-R_j)r_{12}r_{23}}$$

comprises the following steps:

determining the set of Permitted Pairs of integers $(k_j, m_j)$ corresponding to said wavelength $\lambda_j$ ($j=1, 2, \ldots, w$) and said predetermined thickness range according to the relations $m_j = [0.5 + \gamma_j]$, $k_j = (-1)^{[2\gamma_j]}$, $\gamma_j = \frac{2n_2(\lambda_j)}{\lambda_j} t' \cos\theta_2$ ($t_{min} \leq t' \leq t_{max}$), $t' = t(\lambda_j)$, $\cos\theta_2 = (1-\sin^2\theta_1/n_2(\lambda_j)^2)^{\frac{1}{2}}$, where [x] denotes the integral part of a real number x; and determining an array of thickness solutions $t(\lambda_j; k_j; m_j)$ for each of said wavelengths $\lambda = \lambda_j$ $(j=1,2,\ldots,w)$ according to the relation $$t(\lambda_j;k_j;m_j) = \frac{\lambda_j}{4\pi n_2 \cos\theta_2}\left\{k_j\cos^{-1}\left(\frac{R_j(1+r_{12}^2 r_{23}^2) - r_{12}^2 - r_{23}^2}{2(1-R_j)r_{12}r_{23}}\right) + 2\pi m_j\right\}$$

$$\sin\theta_1 = n_2\sin\theta_2 = n_3\sin\theta_3,$$

$$r_{12} = r_{12,k}(\theta_1,\theta_2;\lambda_j),$$

$$r_{23} = r_{23,k}(\theta_2,\theta_3;\lambda_j),$$

where $(k_j, m_j)$ is a pair of integers that is varied over the set of Permitted Pairs for the wavelength $\lambda_j$ and the predetermined thickness range.

3. A method for determining the unknown thickness t, within a predetermined thickness range $t_{min} \leq t \leq t_{max}$, of a film of material with predetermined indices of refraction $n_2 = n_2(\lambda_j)$ $(j=1,2,\ldots,w)$ at a plurality of w distinct wavelengths $\lambda = \lambda_1, \lambda_2, \ldots, \lambda_w$ of light used to illuminate the film, where the film is at least partially transparent to light at each of those wavelengths, where the film is attached on one of its faces to a solid substrate of predetermined material having predetermined indices of refraction $n_3 = n_3(\lambda_j)$ at the plurality of wavelengths $\lambda_j = \lambda_1, \lambda_2, \ldots, \lambda_w$, where the coefficient of amplitude reflection of a light beam of polarization index $k(=p,s)$ and wavelength $\lambda_j$ that is approaching an interface of vacuum and film within the vacuum at incidence angle $\theta_1'$ and with transmission angle within the film of $\theta_2'$ is a predetermined number $r_{12} = r_{12,k'}(\theta_1', \theta_2'; \lambda_j)$, and where the coefficient of amplitude reflection of a light beam of polarization index $k'(=p,s)$ and wavelength $\lambda_j$ that is approaching an interface of film and substrate within the film at incidence angle $\theta_2'$ and with transmission angle $\theta_3'$ is a predetermined number $r_{23} = r_{23,k'}(\theta_2', \theta_3'; \lambda_j)$, the method comprising the steps of:

directing a beam of light of polarization index $k(=p,s)$ at each of the wavelengths $\lambda_1, \lambda_2, \ldots, \lambda_w$ and at a predetermined, nonnegative incidence angle $\theta_1$ at the vacuum-film interface within the vacuum;

measuring the total reflectivity $R'_j = R(\theta_1; \lambda_j)$ $(j=1,2,\ldots,w)$ of the film/substrate at incidence angle $\theta_1$ at each of the wavelengths $\lambda_j = \lambda_1, \lambda_2, \ldots, \lambda_w$;

choosing an array of film thickness values $t_1, t_2, \ldots, t_M$ with $t_{min} \leq t_1 < t_2 < \ldots < t_M \leq t_{max}$;

generating an array $R(\theta_1; \lambda_j; t_s)$ of computed reflectivity numbers for each wavelength $\lambda_j = \lambda_1, \lambda_2, \ldots, \lambda_w$ and each film thickness $t_s = t_1, t_2, \ldots, t_M$ according to the relation $$R(\theta_1;\lambda_j;t_s) = \frac{r_{12}^2 + 2r_{12}r_{23}\cos\beta + r_{23}^2}{1 + 2r_{12}r_{23}\cos\beta + r_{12}^2 r_{23}^2},$$

$$\beta = \frac{4\pi n_2(\lambda_j)t_s}{\lambda_j}\cos\theta_2,$$

$$\sin\theta_1 = n_2\sin\theta_2 = n_3\sin\theta_3;$$

$$r_{12} = r_{12,k}(\theta_1,\theta_2;\lambda_j),$$

$$r_{23} = r_{23,k}(\theta_2,\theta_3;\lambda_j);$$

forming an array of variance numbers $$\chi_R(t_s) = \frac{1}{w}\left[\sum_{j=1}^{W}(R(\theta_1;\lambda_j;t_s) - R'(\theta_1;\lambda_j))^2\right]^{\frac{1}{2}}$$

for $s = 1, 2, \ldots, M$; and choosing as the thickness t of the film the value $t_s$ from the array of film thickness values for which the variance $\chi_R(t_s)$ is a minimum.

4. A method for determining the refractive index $n_2$ of a film of material from a sequence $\{r_{meas}^{(i)}\}_{j=1}^{M_i}$ ($M \geq 1$) of measured values of reflectivity $R_{meas}^{(i)} = R_{meas}(\lambda; \theta_1; i; t_i; k_i; n_3; \theta_3)$ at a sequence of predetermined combinations of film thickness $t_i$, incidence angle $\theta_{1,i}$ and beam polarization index $k_i$ ($=p$ or s), where each film is mounted on a substrate of known refractive index $n_3 = n_3(\lambda)$ and the exposed surface of each film of thickness $t_i$ is irradiated by an optical beam of predetermined wavelength $\lambda$ of beam polarization index $k_i$ at incidence angle $\theta_{1,i}$, the method comprising the steps of:

choosing a sequence, preferably monotonically increasing or monotonically decreasing, $\{n_{2,j}\}_{j=1}^{N}$ of realistic values of the refractive index and computing a corresponding sequence $\{\theta_{2,j}\}_{j=1}^{N}$ of values of refraction angle $\theta_2$ substantially according to the equation $$\cos\theta_2 = [1 - \sin^2\theta_1/n_2^2]^{\frac{1}{2}};$$

forming the functional values $$R_{ij} = R(\theta_{1,i};\lambda;t_i;k_i;n_2 = n_{2,j};\theta_2 = \theta_{2,j};n_3;\theta_3)$$

$(i = 1,2,\ldots,M; j = 1,2,\ldots,N)$ $$R(\theta;\lambda;t;k;n_2;\theta_2;n_3;\theta_3) = \frac{r_{12}^2 + r_{23}^2 + 2r_{12}r_{23}\cos\beta}{1 + 2r_{12}r_{23}\cos\beta + r_{12}^2 r_{23}^2},$$

$$\beta = 4\pi n_2 t \cos\theta_2/\lambda,$$

$$n_1\sin\theta_1 = n_2\sin\theta_2 = n_3\sin\theta_3 \;(n_1 \approx 1),$$

$$r_{12,k=p} = \frac{n_2\cos\theta_1 - n_1\cos\theta_2}{n_2\cos\theta_1 + n_1\cos\theta_2},$$

$$r_{23,k=p} = \frac{n_3\cos\theta_2 - n_2\cos\theta_3}{n_3\cos\theta_2 + n_2\cos\theta_3},$$

$$r_{12,k=s} = \frac{-n_2\cos\theta_2 - n_1\cos\theta_1}{n_2\cos\theta_2 + n_1\cos\theta_1},$$

$$r_{23,k=s} = \frac{-n_3\cos\theta_3 - n_2\cos\theta_2}{n_3\cos\theta_3 + n_2\cos\theta_2},$$

forming the sums $$S_j = \sum_{i=1}^{N}|R_{meas}^{(i)} - R_{ij}|^h \;(j = 1,2,\ldots,N)$$

where h is a predetermined positive real number;

determining the integer or integers $j=J$ for which $S_j = J$ is the minimum of all values in the sequence $\{S_j\}_{j=1}^{N}$; and choosing $n_2 = n_{2,J}$ as the refractive index of the film.

5. A method for determining the refractive index $n_2$ of a material from measured values $R_{meas}^{(1)}, R_{meas}^{(2)}, \ldots, R_{meas}^{(M)}$ of the optical reflectivity of a substantially planar film of the material mounted on a substrate of known material at $M \geq 1$ combinations of film thickness and optical beam incidence angle $\{(t_j, \theta_{1,j})\}_{j=1}^{M}$ for a predetermined optical beam polarization and a predetermined optical beam wavelength $\lambda$ and known refractive index $n_3(\lambda)$ of the substrate material, the method comprising the steps of:

choosing an initial estimated value $n_{2,o}$ for the refractive index $n_2$;

computing the functional values $$f_j(n_2 = n_{2,0}) = R(\theta_{1,j};\lambda;t_j;n_{2,0}) - R_{meas}^j \quad (j = 1,2,\ldots,M)$$

$$R(\theta_1;\lambda;t,n_2) = 1 - (1 - r_{12}^2)(1 - r_{23}^2)/[1 - 2r_{12}r_{23}\cos\beta + r_{12}^2 r_{23}^2]$$

$$\cos\beta = 4\pi n_2 t \cos\theta_2/\lambda,$$

$$\cos\theta_2 = [1 - \sin^2\theta_1/n_2^2]^{\frac{1}{2}},$$

$$\cos\theta_3 = [1 - \sin^2\theta_1/n_3^2]^{\frac{1}{2}},$$

$$r_{12} = \frac{n_2\cos\theta_1 - n_1\cos\theta_2}{n_2\cos\theta_1 + n_1\cos\theta_2} \quad \text{(p-polarization beam)}$$

$$= \frac{n_1\cos\theta_1 - n_2\cos\theta_2}{n_1\cos\theta_1 + n_2\cos\theta_2} \quad \text{(s-polarization beam)}$$

$$r_{23} = \frac{n_3\cos\theta_2 - n_2\cos\theta_3}{n_3\cos\theta_2 + n_2\cos\theta_3} \quad \text{(p-polarization beam)}$$

$$= \frac{n_2\cos\theta_2 - n_3\cos\theta_3}{n_2\cos\theta_2 + n_3\cos\theta_3} \quad \text{(s-polarization beam);}$$

forming the sums $$S^{(1)}(n_2) = \sum_{j=1}^{M} \left( f_j \frac{\partial f_j}{\partial n_2} \right)$$

$$S^{(2)}(n_2) = \sum_{j=1}^{M} \left( f_j \frac{\partial^2 f_j}{\partial n_2^2} + \left(\frac{\partial f_j}{\partial n_2}\right)^2 \right);$$

determining a new estimate $n_{2,i+1}$ ($i=0,1,2,\ldots$) for the film refractive index substantially by the relation $$n_{2,i+1} = n_{2,i} - \frac{1}{\eta} \frac{S^{(1)}(n_2 = n_{2,i})}{S^{(2)}(n_2 = n_{2,i})}$$

where $\eta \geq 1$ is a predetermined real number;

repeating steps 2, 3 and 4 above for $i=0,1,2,\ldots,I$, where $i=I$ is the first positive integer for which $$|n_{2,i+1} - n_{2,i}| \leq \epsilon$$

for a predetermined positive number $\epsilon$; and choosing $n_2 = n_{2,I+1}$ as the refractive index of the film.

6. A method for determining the refractive index $n_2$ of a material from measured values $R_{meas}^{(1)}, R_{meas}^{(2)}, \ldots, R_{meas}^{(M)}$ of the optical reflectivity of a substantially planar film of the material mounted on a substrate of known material at $M \geq 1$ combinations of film thickness and optical beam incidence angle $\{(t_j,\theta_{1,j})\}_{j=1}^{M}$ for a predetermined optical beam polarization and a predetermined optical beam wavelength $\lambda$ and known refractive index $n_3(\lambda)$ of the substrate material, the method comprising the steps of:

choosing an initial estimated value $n_{2,o}$ for the refractive index $n_2$;

computing the functional values $$f_j(n_2 = n_{2,0}) = R(\theta_{1,j};\lambda;t_j;n_{2,0}) - R_{meas}^j \quad (j = 1,2,\ldots,M)$$

$$R(\theta_1;\lambda;t,n_2) = 1 - (1 - r_{12}^2)(1 - r_{23}^2)/[1 - 2r_{12}r_{23}\cos\beta + r_{12}^2 r_{23}^2]$$

$$\cos\beta = 4\pi n_2 t \cos\theta_2/\lambda,$$

$$\cos\theta_2 = [1 - \sin^2\theta_1/n_2^2]^{\frac{1}{2}},$$

$$\cos\theta_3 = [1 - \sin^2\theta_1/n_3^2]^{\frac{1}{2}},$$

$$r_{12} = \frac{n_2\cos\theta_1 - n_1\cos\theta_2}{n_2\cos\theta_1 + n_1\cos\theta_2} \quad \text{(p-polarization beam)}$$

$$= \frac{n_1\cos\theta_1 - n_2\cos\theta_2}{n_1\cos\theta_1 + n_2\cos\theta_2} \quad \text{(s-polarization beam)}$$

$$r_{23} = \frac{n_3\cos\theta_2 - n_2\cos\theta_3}{n_3\cos\theta_2 + n_2\cos\theta_3} \quad \text{(p-polarization beam)}$$

$$= \frac{n_2\cos\theta_2 - n_3\cos\theta_3}{n_2\cos\theta_2 + n_3\cos\theta_3} \quad \text{(s-polarization beam);}$$

forming the sums $$S^{(1)}(n_2) = \sum_{j=1}^{M} \left( f_j \frac{\partial f_j}{\partial n_2} \right) + \left[ \left( \sum_{j=1}^{M} \left( f_j \frac{\partial f_j}{\partial n_2} \right) \right)^2 - \right.$$

$$\left. \sum_{k=1}^{M} \left( f_k \frac{\partial^2 f_k}{\partial n_2^2} + \left(\frac{\partial f_k}{\partial n_2}\right)^2 \right) \right]^{\frac{1}{2}},$$

$$S^{(2)}(n_2) = \sum_{m=1}^{M} \left[ f_m \frac{\partial^2 f_m}{\partial n_2^2} + \left(\frac{\partial f_m}{\partial n_2}\right)^2 \right];$$

determining a new estimate $n_{2,i+1}$ ($i=0,1,2,\ldots$) for the film refractive index substantially by the relation $$n_{2,i+1} = n_{2,i} - \frac{1}{\eta} \frac{S^{(1)}(n_2 = n_{2,i})}{S^{(2)}(n_2 = n_{2,i})}$$

where $\eta \geq 1$ is a predetermined real number;

repeating steps 2, 3 and 4 above for $i=0,1,2,\ldots,I$, where $i=I$ is the first positive integer for which $$|n_{2,i+1} - n_{2,i}| \leq \epsilon$$

for a predetermined positive number $\epsilon$; and choosing $n_2 = n_{2,I+1}$ as the refractive index of the film.

7. A method for determining the refractive index $n_2$ of a $\phi = 4\pi t/\lambda$; reflectivity at a predetermined wavelength $\lambda$ of a substantially planar film of known film thickness $t$ of the material, mounted on a substantially planar substrate of known substrate refractive index $n_3(\lambda)$, the method comprising the steps of:

irradiating the exposed surface of the film with an optical beam of s-wave beam polarization and wavelength $\lambda$ at a predetermined incidence angle $\theta_1$ and measuring the reflectivity $R_{meas}$ of the film;

forming the ratios $\psi_{13} = \cos\theta_1/[n_3(\lambda)^2 - \sin^2\theta_1]$, and $\theta = 4\rho t/\lambda$;

solving the equation $$\psi_{13}^2(1 - \cos\phi Z)Z^4 - [(1 + \psi_{13}^2)(1 + \cos\phi Z) -$$

$$4\psi_{13}((1 + R_{meas})/(1 - R_{meas}))]Z^2 = (1 - \cos\phi Z) = 0$$

for all real positive roots $\hat{z}$ in a predetermined interval on the positive real axis; and determining $n_2$ substantially as $$n_2 = [(\hat{z}\cos\theta_1)^2 + \sin^2\theta_1]^{\frac{1}{2}}.$$

* * * * *